(12) United States Patent
Melendez et al.

(10) Patent No.: US 6,374,845 B1
(45) Date of Patent: Apr. 23, 2002

(54) SYSTEM AND METHOD FOR SENSING AND CONTROLLING BEVERAGE QUALITY

(75) Inventors: Jose L. Melendez, Plano; Richard A. Carr, Rowlett; Jerome L. Elkind, Richardson, all of TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 09/549,287

(22) Filed: Apr. 14, 2000

Related U.S. Application Data

(60) Provisional application No. 60/132,286, filed on May 3, 1999.

(51) Int. Cl.⁷ .............................................. G05D 11/13
(52) U.S. Cl. .................................. 137/3; 137/9; 137/93
(58) Field of Search ............................. 137/3, 7, 9, 93, 137/88

(56) References Cited

U.S. PATENT DOCUMENTS

| | | | |
|---|---|---|---|
| 2,868,216 A | * 1/1959 | Robertson | 137/93 X |
| 4,986,497 A | * 1/1991 | Susko | 137/93 |
| 5,398,711 A | * 3/1995 | Ardrey, Jr. | 137/5 |
| 5,925,878 A | * 7/1999 | Challener | 250/225 |
| 6,135,319 A | * 10/2000 | Camezon | 222/129.1 X |

* cited by examiner

*Primary Examiner*—Stephen M. Hepperle
(74) *Attorney, Agent, or Firm*—Dwight N. Holmbo; Wade James Brady, III; Frederick J. Telecky, Jr.

(57) ABSTRACT

Disclosed is a method of automatically sensing and controlling beverage quality for soft drinks from a fountain dispenser, for example, comprising the steps of supplying a first fluid, such as water or carbonated water, wherein the flow of the first fluid is controlled by a first valve, supplying a second fluid, mixing the first fluid and the second fluid, passing a sample of the mixture of the first fluid and the second fluid onto a sensing surface of a fixed optic sensor, measuring one or more properties of the sample, such as, for example, refractive index, temperature, and pressure, controlling the first valve based on the one or more properties, and dispensing the mixture. The first valve may be proportionally enlarged and reduced or it may selectively opened and closed pursuant to a desired duty cycle. The present invention further comprises a system for automatically sensing and controlling beverage quality, comprising a controller means, a first valve electrically coupled to the controller means for controlling supply of a first fluid, a second valve electrically coupled to the controller means for controlling supply of a second fluid, and a fixed optic sensor electrically coupled to the controller means.

35 Claims, 3 Drawing Sheets

SYSTEM AND METHOD FOR SENSING AND CONTROLLING BEVERAGE QUALITY

This application claims priority under 35 U.S.C. §119(e)(1) of provisional application No. 60/132,286, filed May 3, 1999.

FIELD OF THE INVENTION

The present invention relates in general to sensor systems and more particularly, to a system and method for sensing and controlling the quality of beverages such as soft drinks.

BACKGROUND OF THE INVENTION

Without limiting the scope of the invention, its background is described in connection with sensing and controlling the quality of beverages such as soft drinks. It should be appreciated by one skilled in the art that the term beverages refers to a variety of fluids and other media, and that the principles of the present invention are applicable to a variety of media.

The dispensing of fountain beverages is presently generally accomplished using either premix systems in which a finished beverage is delivered to a proprietor from a bottler, and postmix systems in which flavored syrup is delivered to the proprietor and mixed with water at the point of delivery.

A premix system generally utilizes product containers filled with finished soft drink which may be under carbon dioxide pressure. In these systems, the product is normally delivered to the consumer via a single orifice dispensing valve. Premix systems are also used in bottling plants which typically operate at extremely high flow rates. These systems are relatively expensive installations and are unsuitable for most typical restaurant settings.

A postmix system generally utilizes flavored syrup combined with carbonated or still water at a prescribed ratio and delivered through a dispensing valve at a fountain having passages for both syrup and water. The valve combines the syrup and water immediately before delivery into a cup on an individual serving basis. The valves are typically adjusted periodically to alter the mix ratio of the ingredients of the beverage.

In the restaurant industry, the valves that control the delivery of the beverage constituents are typically manually adjusted after a taste test of the finished beverage or a customer's complaint, for example. The decision to alter the composition of the beverage is a highly subjective one, and is typically based on the operator's subjective preference regarding the desired taste or sweetness of the beverage. In addition, the manual adjustment of the valves significantly lacks precision and accuracy. It is furthermore highly susceptible to human error, and is therefore inherently unreliable and inaccurate. The manual adjustments are also time-consuming and cumbersome.

Various attempts at maintaining a consistent ratio of the components of the beverages offered at a soft drink fountain dispenser have been made in the prior art. In one method, predetermined volumes of syrup and carbonated water are measured in a container called a brixing cup. "Brix," as understood by those skilled in the art, is the percent concentration of sugar. Proper brixing is determined by ratio marks on the brixing cup.

The brixing method must be periodically repeated in order to account for any long term changes in the pressures or viscosities of the dispensed fluid. Short term variations in flow rates during a single dispensing operation, or between individual dispensing operations, cannot be accounted for by periodic manual adjustments.

In another method, the rate of flow of the syrup and carbonated water are measured with flow-meters. The flow rates are adjusted and operate at a prescribed ratio. A flexible flow washer may be positioned in a flow line, and variations in fluid flow rate cause the opening of the washer to become enlarged or constricted. This method is flawed in that it does not account for factors contributing to variations in the accuracy of the mix ratio, such as changes in fluid viscosity. This method also lacks any significant degree of accuracy and is therefore unreliable.

SUMMARY OF THE INVENTION

The methods in the prior art all suffer in accuracy and reliability because they do not measure the actual product that is finally dispensed from the fountain. Inaccuracy in the ratio of the beverage constituents results in inconsistency and undesirable variations in the quality and taste of the beverages. For example, dispensers that have poor accuracy and reliability may dispense a beverage that is too sweet or not sweet enough, or a carbonated soda that is flat. Variations from the desired mix accuracy also result in uneconomical use of the syrup.

In addition, none of the methods in the prior art provide for real-time sampling of the beverage as it is being dispensed. The prior art methods are also inefficient and costly, due to their time-consuming nature and their potential to make inefficient use of resources of syrup by unnecessarily adding excessive amounts of syrup. Furthermore, many of the devices in the prior art are incompatible with previously manufactured beverage dispensers.

Another problem with the prior art systems is that they do not ensure the cleanliness of the machines, particularly the dispensing nozzle. It is difficult and cumbersome to clean the nozzles thoroughly. Each nozzle is typically manually cleaned on a very irregular and sporadic basis, or neglected all together. Manually cleaning each nozzle is time-consuming, cumbersome, and ineffective. Bacteria and other unwanted germs can grow anywhere the syrup and water are mixed. The flow lines in the dispensing system are typically neglected and are therefore unsanitary. The residue of the beverages on the nozzles also attracts roaches, ants and other insects. Thus, the failure to regularly and thoroughly clean the parts of the dispenser where beverages are mixed can lead to contaminated beverages being served and consumed by customers of a restaurant, which poses a serious health risk.

A need has therefore arisen for a system and method for sensing and controlling the quality of beverages that overcomes the limitations in the prior art. A system and method that provide for accurate monitoring and improvement of beverage quality would have great advantages over the prior art. A system that may be retrofitted to existing beverage dispensing systems and that can interface with existing beverage dispensing systems would be highly desirable as well. A system and method that allows for remote reporting and control would also be advantageous over the prior art. A system and method that are able to detect poor operation and prevent system failure before it occurs would also be desirable.

The present invention comprises a method of automatically sensing and controlling beverage quality, comprising the steps of supplying a first fluid, wherein the flow of the first fluid is controlled by a first valve, supplying a second fluid, mixing the first fluid and the second fluid, passing a sample of the mixture of the first fluid and the second fluid onto a sensing surface of a fixed optic sensor, measuring one or more properties of the sample, controlling the first valve based on the one or more properties, and dispensing the mixture into a receptacle. The present invention further comprises a system for automatically sensing and controlling beverage quality, comprising a controller means, a first valve electrically coupled to the controller means for controlling supply of a first fluid, a second valve electrically coupled to the controller means for controlling supply of a second fluid, and a fixed optic sensor electrically coupled to the controller means.

For a more complete understanding of the present invention, including its features and advantages, reference is now made to the following detailed description, taken in conjunction with the accompanying drawings.

BRIEF DESCRIPTION OF THE DRAWINGS

In the drawings.

Corresponding numerals and symbols in the different figures refer to corresponding parts unless otherwise indicated.

DETAILED DESCRIPTION OF THE PREFERRED EMBODIMENT

Figure 1:
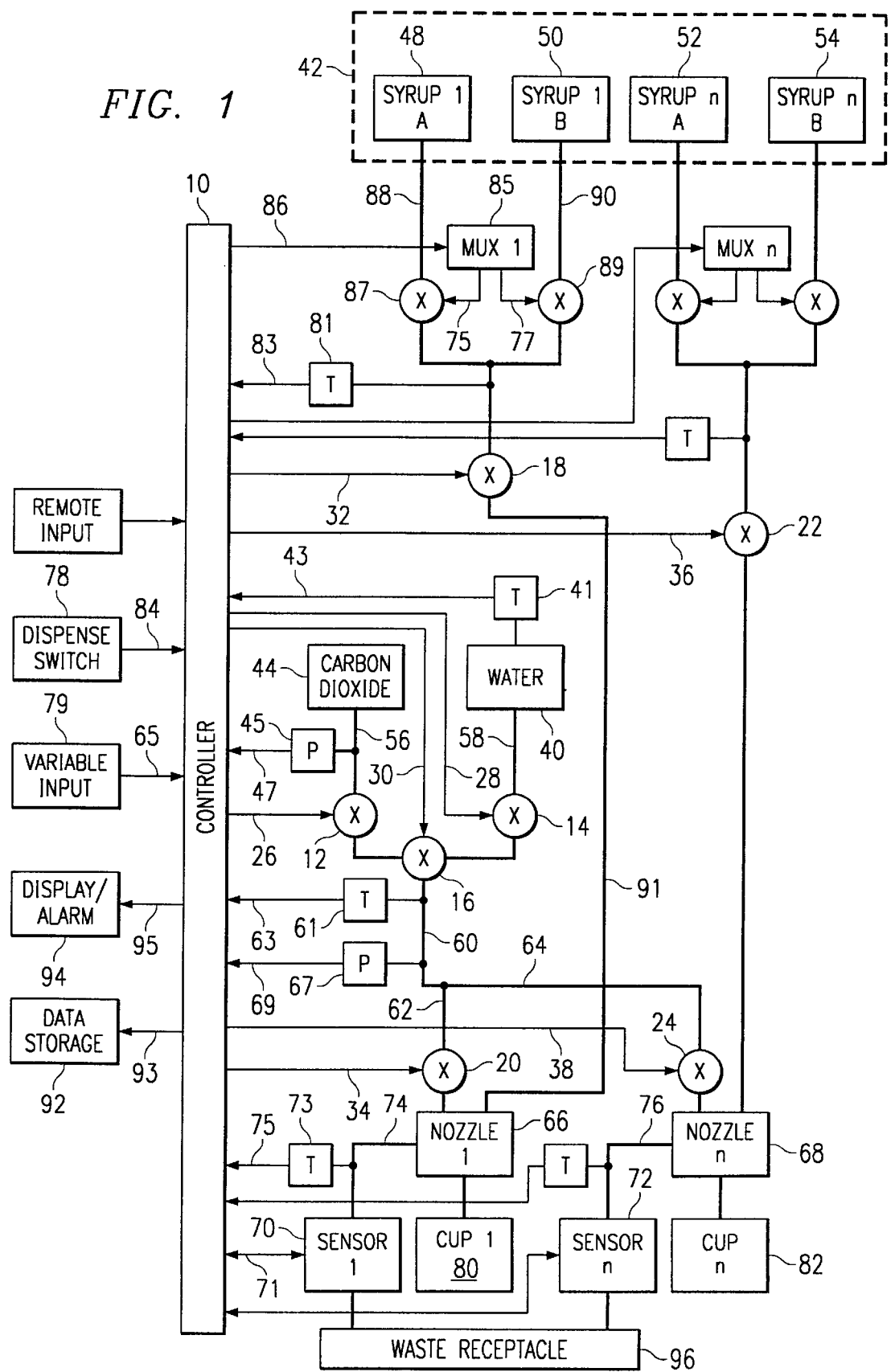
FIG. 1 depicts a block diagram of a system for sensing and controlling the quality of beverages in accordance with the present invention.

Reference is now made to FIG. 1 in which a block diagram of a system for sensing and controlling the quality of a medium such as a carbonated soft drink in accordance with one embodiment of the present invention is depicted.

The system of the present invention includes a controller 10 coupled to a plurality of electrically operated valves 12, 14, 16, 18, 20, 22 and 24 via electrical interfaces 26, 28, 30, 32, 34, 36, and 38, respectively, as shown in FIG. 1. Electrically operated valves 12, 14, 16, 18, 20, 22 and 24 may be a fluttering valve that opens and closes, or a proportional valve which allows for changes in diameter of the orifice of the valve. The system further includes a water supply 40, one or more flavored syrup supplies 42, and may include a carbon dioxide supply 44 for making carbonated soft drink beverages. The system may also comprise a refrigeration system for keeping the liquids chilled, and an ice dispenser (not shown).

The temperature of the water in water supply 40 may be monitored by a temperature sensor 41. Temperature sensor 41 may comprise a thermistor, thermocouple or other temperature measuring device. Temperature sensor 41 may send data via electrical interface 43 to controller 10 relating to the temperature measurements of the water in water supply 40.

The pressure of the carbon dioxide released from carbon dioxide supply 44 may be monitored by a pressure sensor 45. Pressure sensor 45 may send data via electrical interface 47 to controller 10 relating to the pressure measurements of the carbon dioxide released from carbon dioxide supply 44.

As shown in FIG. 1, the system of the present invention may comprise n syrup supplies for n flavors of drinks available to be dispensed. Syrup supply 48 (1A) and alternate syrup supply 50 (1B) represent one particular flavor of syrup, and syrup supply 52 (nA) and alternate syrup supply 54 (nA) represent the nth flavor of syrup. For each flavor of syrup, there is provided a sensor for sensing one or more properties of a sample of the beverage. As shown in FIG. 1, sensor 70 is provided for sensing properties of a beverage flavored with a first flavor of syrup, while sensor 72 is provided for sensing properties of a beverage flavored with the nth flavor of syrup.

Controller 10 may be a microcontroller or digital signal processing unit, such as TMS320F206 or TMS320F243, manufactured by Texas Instruments. When controller 10 opens electrically operated valve 12, a predetermined amount of carbon dioxide from carbon dioxide supply 44 is drawn into an inlet or flow line 56. When controller 10 opens electrically operated valve 14, a predetermined amount of water from water supply 40 is drawn into a flow line 58. When controller 10 opens electrically operated valve 16, a predetermined amount of carbonated water is drawn into a flow line 60 for a predetermined length of time. Flow line 60 branches into n branches of flow lines. For ease of illustration, flow line 60 is shown in FIG. 1 as branching into flow line 62 and flow line 64.

The temperature of the carbonated water in flow line 60 may be monitored by a temperature sensor 61. Temperature sensor 61 may comprise a thermistor, thermocouple or other temperature measuring device. Temperature sensor 61 may send data via electrical interface 63 to controller 10 relating to the temperature measurements of the carbonated water in flow line 60.

The pressure of the carbonated water in flow line 60 may be monitored by a pressure sensor 67. Pressure sensor 67 may send data via electrical interface 69 to controller 10 relating to the pressure measurements of the carbonated water in flow line 60. Alternatively, the pressure of the carbonated water may be determined by optically counting the number of bubbles in the carbonated water.

Prior to the dispensing of beverages, controller 10 may open electrically operated valves 12, 14, 16, 20 and 24 to allow carbonated water to be drawn through flow lines 62 and 64 to initially rinse each said flow line and each nozzle 66 and 68. This may occur daily at a prescribed time; for example, where a dispensing system is located in a restaurant, rinsing may occur each night while the restaurant is closed. Alternatively, a cleansing agent (not shown) such as a detergent or solvent may be drawn through flow lines 62 and 64 for cleaning each said flow line and each nozzle 66 and 68. The cleansing agent may also used to clean a sensing surface of each sensor 70 and 72.

Each sensor 70 and 72 may be located within nozzle 66 and 68, respectively for the measurement of one or more properties of a sample of the beverage to be dispensed, such as refractive index, pressure, temperature and viscosity, for example. Alternatively, a sample of a beverage may be drawn through a flow line 74 and introduced to a sensing surface of sensor 70. Similarly, a sample of an n-flavored beverage may be drawn through a flow line 76 and introduced to a sensing surface of sensor 72. It should be understood, however, that many varying arrangements of sensor 70 and 72 may be employed consistent with the present invention.

Figure 2:
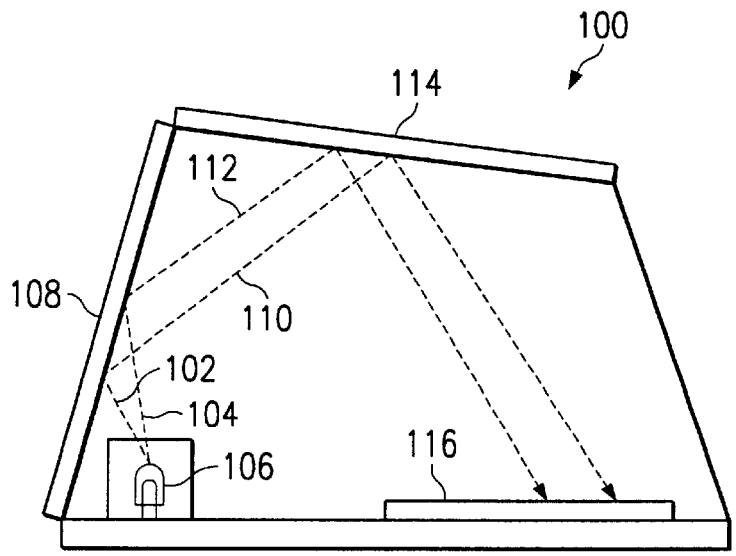
FIG. 2 depicts a schematic diagram of an exemplary fixed optic surface plasmon resonance sensor in accordance with the present invention.

Sensor 70 is preferably a surface plasmon resonance fixed optic sensor generally depicted as 100 in FIG. 2. A surface plasmon, as known in the art, is a surface charge density wave at the surface of a dielectric interface having a thin conductive film formed thereon. The oscillation of free electrons at a conductor-dielectric boundary is affected by the refractive index of the material adjacent to the film. Using a polarized beam of monochromatic light, surface plasmon polaritons can be excited. Resonance occurs when the polarized light is totally internally reflected from the conductive film. The light internally reflected from the film has a minimum intensity at the resonance angle. By detecting the resonance angle, the refractive index of a material adjacent to the film may be determined, which is indicative of other properties of the material. A more detailed description of surface plasmon resonance may be found in the article "Surface Plasma Oscillations and Their Applications," Rather, H., *Physics of Thin Films,* 1977.

In accordance with fixed optic surface plasmon resonance sensor 100, polarized light rays 102 and 104 emanating from a monochromatic light source 106 strike a sensing surface 108. The precise composition of sensing surface 108 may be tailored according to the specifications of the user and the composition of the material being tested. Components 110 and 112 of the light rays 102 and 104 may be transmitted from the sensing surface 108 onto a reflective surface 114, and are then reflected onto a photodetector 116. The reflective surface 114 may be a mirror that is flat, or may be concave or convex.

For measuring optical radiation, a suitable photodetector 116 has an array of discrete photosensing areas, or pixels. Light energy striking a pixel generates electron-hole pairs in the region under the pixel. The field generated by the bias on the pixel causes the electrons to collect in the element while the holes are swept into the substrate. Each sensing area in photodetector 116 thereby produces a signal on an output with a voltage that is proportional to the intensity of the light striking photodetector 116. This intensity and its corresponding voltage are at their maxima in the total internal reflection region. When fixed optic surface plasmon resonance sensor 100 serves as quality control sensor 34 of FIG. 1, the output, representing bit level data from photodetector 116, is transmitted to controller 10.

Figure 3:
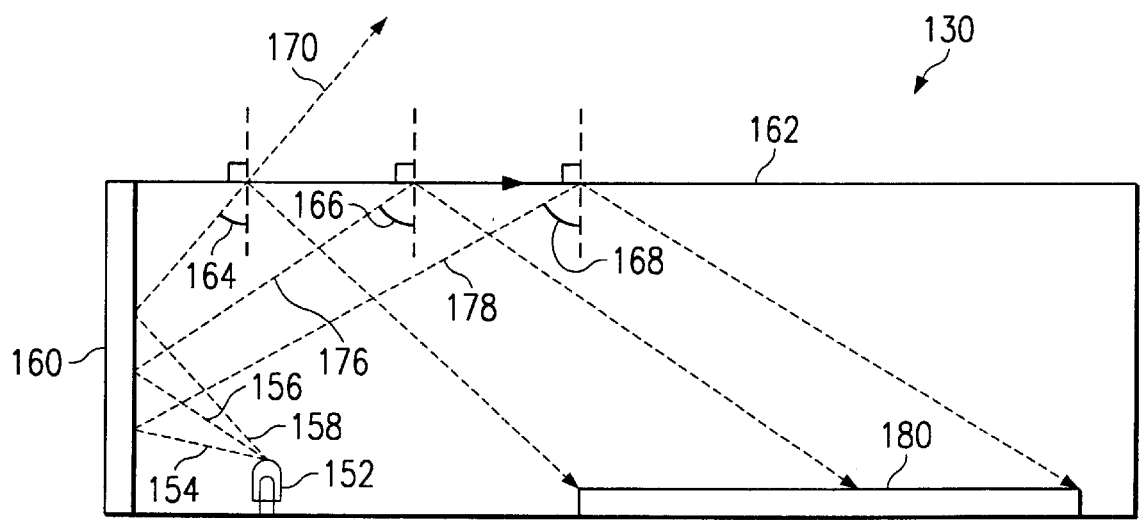
FIG. 3 depicts a schematic diagram of an exemplary fixed optic critical angle sensor in accordance with the present invention.

Alternatively, sensor 70 may be a refractometer such as a fixed optic critical angle sensor generally depicted as 130 in FIG. 3. Since refractive index is a function of critical angle, determination of the critical angle gives rise to determination of the refractive index of the sample, which is indicative of one or more sample properties, from which further qualitative and quantitative analyses about the quality of the sample may be made.

In accordance with fixed optic critical angle sensor 130, when light rays are directed to the sample at angles of incidence smaller than the critical angle, a portion of the light is refracted into the sample, resulting in an overall loss. At angles of incidence larger than the critical angle, total internal reflection occurs, and the full intensity of the light is reflected off the sample. The critical angle, and consequently the refractive index, may be then determined by measuring the intensities of the reflected light rays, and detecting a transition from a high intensity to a low intensity.

Fixed optic critical angle sensor 130 thus detects critical angle to find the sample's refractive index, as shown in Equation 1 below, where $n_2$ is the index of refraction of the medium of the sample, $n_1$ is the index of refraction of the medium of origin and $_c$ is the critical angle.

$$n_2 = (n_1)(\sin {}_c).$$  Eq. 1

As shown in FIG. 3, a light source 152 emits light rays, 154, 156, and 158 toward a mirrored surface 160. The light rays 154, 156 and 158 then travel in the direction of a sensing surface 162 which forms the interface between fixed optic critical angle sensor 130 and the sample. Thus, the sensing surface 162 is in direct contact with the sample.

The light rays 154, 156 and 158 strike sensing surface 162 at angles 164, 166 and 168, respectively. For angles of incidence smaller than the critical angle 166, a portion of the light is refracted into the sample, resulting in an overall loss. This is illustrated by refracted ray 170 which travels into the sample and reflected ray 172 which is reflected toward a photodetector 180.

At the critical angle 166, a light ray 174 reflects along sensing surface 162 at a 90° angle of refraction, minimizing the overall loss of light into the sample. Thus, the critical angle 166 can be measured as the angle measured between the incident light ray 176 and the normal to sensing surface 162. For angles of incidence larger than the critical angle 166, such as 168, the incident ray 178 is totally internally reflected, with no refracted component, and its full intensity is directed toward photodetector 180.

Light energy striking a pixel of photodetector 180 generates electron-hole pairs in the region under the pixel. The field generated by the bias on the pixel causes the electrons to collect in the element while the holes are swept into the substrate. Each sensing area in photodetector 180 thereby produces a signal on an output with a voltage that is proportional to the intensity of the light striking photodetector 180. This intensity and its corresponding voltage are at their maxima in the total internal reflection region.

It is desirable to have the light rays strike photodetector 180 at angles as close as possible to 90°. By shaping fixed optic critical angle sensor 130 such that light strikes the photodetector 180 at an angle close to 90°, photodetector 180 will have the maximum possible sensitivity. It should be understood, however, that many configurations of fixed optic critical angle sensor 130 may be employed consistent with the present invention.

As described, a range of angles of the reflected light rays are projected onto photodetector 180. The critical angle is marked by a transition from high to low. When fixed optic critical angle sensor 130 serves as sensor 70 of FIG. 1, the output, representing bit level data from photodetector 180, is transmitted to controller 10 for further qualitative and/or quantitative analysis.

Referring again to FIG. 1, fixed optic sensing as described with respect to FIGS. 2 and 3 is preferably used to achieve precise ratios of syrup, carbon dioxide and water for consistently creating a carbonated beverage of a desired brix and quality. Prior to dispensing, a solution having known, well-characterized properties may be initially drawn and passed over each sensor 70 and 72 in order to calibrate the system. For example, cold water at a specific temperature may be used to calibrate each sensor 70 and 72. In addition, a high quality soft drink, from a bottle, for example, at a known level of brix may be used to calibrate each sensor 70 and 72.

The dispensing process is initially enabled by switching a dispense switch 78 to its "on" state for a desired flavor of beverage. Dispense switch 78 may be a conventional push button device, or a tab-like trigger, for example. Alternatively, dispense switch 78 may comprise a sensor which senses the placement of a cup 80 (or cup 82) beneath its corresponding nozzle 66 (or nozzle 68).

When controller 10 receives indication via electrical interface 84 that dispense switch 78 is on for a particular flavor of beverage, compilation of the desired flavored beverage begins. For ease of illustration, operation will be described below with reference to selection of syrup flavor #1.

Controller 10 may communicate with a multiplexer 85 via an electrical interface 86. Multiplexer 85 sends a signal via an electrical interface 75 to open an electrically operated valve 87. Accordingly, syrup from syrup supply 48 is drawn into a flow line 88. If syrup supply 48 is empty, multiplexer 85 may be used to send a signal via an electrical interface 77 to open an electrically operated valve 89, and syrup from alternate syrup supply 50 is drawn into a flow line 90. Controller 10 sends a signal via electrical interface 32 to open electrically operated valve 18. The syrup then flows through flow line 91 to be mixed in nozzle 66, and turbulence may be produced therein. The temperature of the syrup may be measured by temperature sensor 81 and transmitted to controller 10 via an electrical interface 83.

At the same time, controller 10 sends a signal to open electrically operated valves 12, 14 and 16 in order to allow carbonated water to flow in flow line 62. Controller 10 may send a signal to open and close electrically operated valve 20 pursuant to a prescribed duty cycle for obtaining a desired percent composition of carbonated water in the final beverage. Controller 10 may optionally send a signal to open and close electrically operated valve 18 pursuant to a prescribed duty cycle for obtaining a desired percentage of syrup, for acquiring the desired brix. Alternatively, controller 10 may send signals to open electrically operated valve 18 at a variable diameter.

The period of the duty cycle for each constituent is preferably relatively short such that the cycle is repeated many times during the dispensing of each drink. For example, where the total length of time to dispense a drink into a cup of known volume is approximately 10 seconds, a period of approximately 1 second or less may be suitable.

The desired brix may be a predetermined default value stored in controller 10, or alternatively, may be varied according to the operator's preference. In accordance with the present invention, a variable input 79 communicates with controller 10 via an electrical interface 65. Variable input 79 may comprise a conventional push button, control knob, or keypad input, for example, to enable the operator to adjust the determined end point of quality or sweetness. Variable control input 79 thus allows the operator to exercise discretion in determining what level of quality or sweetness is deemed unacceptable.

In accordance with the present invention, carbonated water from flow line 62 is combined with the syrup from flow line 91, mixed in nozzle 66 and dispensed into cup 80. The mixing in nozzle 66 may be accomplished by simply introducing the constituents to each other, or they may be more thoroughly mixed with the introduction of turbulence, for example. At the same time, a representative sample of the mixed beverage is passed over the sensing surface of sensor 70. One or more properties of the sample such as refractive index, for example, is measured and transmitted to controller 10 via an electrical interface 71. The temperature of the sample may be measured by temperature sensor 73 and transmitted to controller 10 via an electrical interface 75.

Data relating to the properties of the sample is also transmitted from controller 10 to a data storage device 92 via an interface 93. Controller 10 may also be communicably linked to a network to enable such data to be transmitted to a remote data storage unit. Controller 10 may also be communicably linked to a remote input that provides instructions for controlling the operation of controller 10.

If the refractive index is outside an acceptable range of values corresponding to a desired range of brix values, then the ratio of the carbonated water and the syrup may be adjusted in order to compensate for the discrepancy. The adjustment may be accomplished by modifying the duty cycle such that a given valve is on or off for a different length of time, or by adjusting the diameter of a given valve to either increase or reduce the flow rate. For example, if the refractive index indicates that the beverage is too sweet, controller 10 may increase the percent duty cycle that electrically operated valve 20 is open, in order to effect a reduced concentration of syrup in the end result.

In accordance with conventional statistical process control algorithms known in the art, a weighted average of past data is used to prevent overcompensation of values outside of the regular control range. If the refractive index is drastically outside the specifications, then controller 10 sends a signal via electrical interface 95 to an output 94 to trigger an audio-visual alarm indicative of a problem that is not correctable by adjusting duty cycles of the beverage constituents. Output 94 may comprise a light emitting diode (LED) or a display of alphanumeric data. If syrup supply 48 is exhausted, multiplexer 85 may select alternate syrup supply 50 and open electrically operated valve 89 via electrical interface 77 to allow flow of syrup flavor #1 from flow line 90 to flow line 91.

The occurrence of the switch from syrup supply 48 to alternate syrup supply 50 may be recorded in data storage device 92 for inventory control purposes. Recordal of this data at a remote location such as a restaurant's corporate headquarters, would enable automation of requests to ship additional units of syrup, rather than storing large supplies of syrup locally, which is an inefficient use of space and capital.

The properties of the beverage sample are continuously monitored under real-time conditions as long as dispense switch 78 is on. Once the sample is passed over the sensing surface of sensor 70, it may be discarded into waste receptacle 96. In addition, residual overflow from nozzles 66 and 68 may also be discarded into waste receptacle 96, which is typically is located beneath nozzles 66 and 68.

Figure 4:
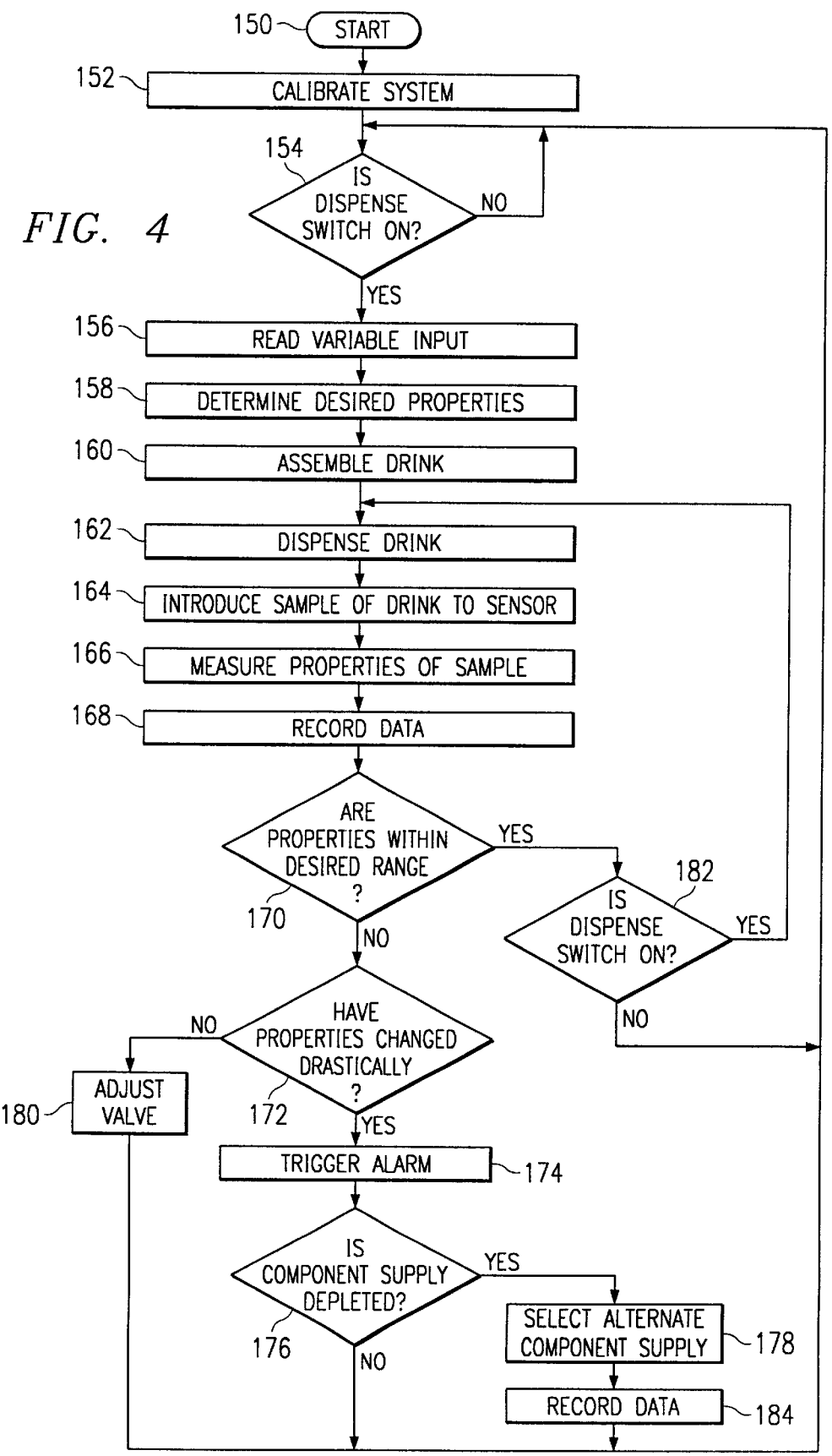
FIG. 4 depicts a flow diagram for a method of sensing and controlling the quality of beverages in accordance with the present invention.

Reference is now made to FIG. 4, in which a flow diagram of a method for sensing and controlling the quality of a beverage in accordance with the present invention is shown. Process flow begins in step 150, and the system is calibrated in step 152. One or more solutions may be passed over the sensing surface of each sensor in step 152. For example, a cleansing agent such as a solvent or detergent may be used to cleanse the surface of the sensor. A known reference or standard such as ice water at a specific, known temperature, or a known high quality sample of a particular soft drink may also be introduced to the sensor to confirm proper operation of the sensor. In addition, a cleansing agent or carbonated water may be initially dispensed in order to clean the flow lines and nozzles.

After calibration in step 152, a controller will continually poll the status of the dispense switch, as indicated in step 154. If the dispense switch is in the "on" state, a controller initially reads data from a variable input setting to determine the desired level of brix in step 156. The variable input allows the operator to adjust the brix in accordance with the operator's subjective preference. Using both the variable input data and standard default values, the desired properties of the beverage are determined in step 158. These properties may include, for example, the desired temperatures of the beverage constituents, the desired refractive index of the beverage to be dispensed and the desired pressure of carbon dioxide. Next, in step 160, the beverage is assembled in accordance with the desired properties and constituent ratios determined previously in step 158. Carbonated water and flavored syrup are thus drawn according to the predetermined ratio. For example, the syrup might be continuously drawn while a valve for allowing flow of the carbonated water is opened and closed by the controller pursuant to its calculated duty cycle. Once the beverage is assembled, it is mixed through a nozzle, for example, and dispensed into a cup or other such drinking receptacle in step 162.

While the beverage is being dispensed, a sample of the beverage may be introduced to a sensor in step 164 for analyzing properties of the sample of the beverage. One method of sampling would be to install the sensor in the dispensing nozzle, allowing the beverage to be sampled while it is being dispensed. Alternatively, the sensor may be apart from the nozzle, and a sample of the beverage may be drawn to the sensing surface.

Once the sample is introduced to the sensor in step 164, the properties of the beverage are measured in step 166. One property that could be measured and used to modify the brix of the beverage is the index of refraction. This measurement would allow the amount of syrup in the beverage to be determined as the beverage is dispensed. Data relating to the properties measured by the sensor are recorded in a data storage device in step 166. Using statistical processes known in the art, a weighted average of past points may be calculated. The system could either store the data over the course of months and years, or simply store data since the dispenser was powered on.

The data is then analyzed to determine if the beverage properties are within a desired range in step 168. For instance, utilizing fixed optic surface plasmon resonance sensing or other fixed optic sensing techniques, the index of refraction of the beverage might be measured and then compared to a low and high tolerance value. If the properties measured are between this low and high value, the system will continue to dispense the beverage with no change in beverage properties as long as the dispense switch is in the on position, as shown in step 182. If, however, the properties are outside of specification, the system will determine if the properties are well outside specification in step 172. If the properties are outside of specification, but not deviating so much as to indicate the complete absence of a particular ingredient, the system will adjust the valve for one or more of the components to compensate for the deviation in step 180.

After adjusting the valve, process flow returns to step 154, and the system will continue dispensing if the dispense switch is on. If the properties measured from the sample are suddenly drastically outside of specification, this may be an indication that one or more of the constituents used to assemble the beverage has been depleted and is no longer available to the system. In this case, beverage dispensing is halted, and an alarm is triggered, notifying the owner or operator of a possible problem in step 174. After triggering an audible or visual alarm, the system will use a fault detection algorithm to determine which component is depleted in step 176. The depleted component is replaced in step 178, either by the system or the operator, by selecting an alternate supply of the depleted component. For example, if the syrup supply is exhausted, a multiplexer may automatically select an alternative source of syrup without disruption to process flow. Data pertaining to the depletion and replacement is recorded onto the data storage device for inventory purposes. After the information has been stored, the system will return to step 154, and the controller polls to see if the dispenser switch is in the on position.

While this invention has been described with reference to illustrative embodiments, this description is not intended to be construed in a limiting sense. Various modifications and combinations of the illustrative embodiments as well as other embodiments of the invention will be apparent to persons skilled in the art upon reference to the description. It is therefore intended that the appended claims encompass any such modifications or embodiments.

What is claimed is:

1. A method of automatically sensing and controlling beverage quality, comprising the steps of:

supplying a first beverage fluid, wherein the flow of said first beverage fluid is controlled by a first valve;

supplying a second beverage fluid;

mixing said first beverage fluid and said second beverage fluid;

passing a sample of the mixture of said first beverage fluid and said second beverage fluid onto a sensing surface of a fixed optic sensor;

measuring one or more properties of said sample;

controlling said first valve based on said one or more properties to maintain a precise and predetermined fixed ratio of the beverage fluids as the one or more properties change; and dispensing said mixture.

2. The method as recited in claim 1 wherein said fixed optic sensor is a surface plasmon resonance sensor.

3. The method as recited in claim 1 wherein said fixed optic sensor is a refractometer.

4. The method as recited in claim 1 wherein said one or more properties comprises refractive index.

5. The method as recited in claim 1 further comprising the step of passing a sample of the mixture of said first fluid and said second fluid over a temperature sensor such that said one or more properties comprises temperature.

6. The method as recited in claim 1 further comprising the step of passing a sample of the mixture of said first fluid and said second fluid over a pressure sensor such that said one or more properties comprises pressure.

7. The method as recited in claim 1 wherein said first fluid comprises water.

8. The method as recited in claim 1 wherein said second fluid comprises a concentrated flavored syrup.

9. The method as recited in claim 1 wherein the diameter of said first valve is variably increased and decreased.

10. The method as recited in claim 1 wherein said first valve is selectively opened and closed according to a prescribed first duty cycle.

11. The method as recited in claim 10 further comprising the step of adjusting said first duty cycle.

12. The method as recited in claim 1 wherein the flow of said second fluid is controlled by a second valve.

13. The method as recited in claim 1 further comprising the step of triggering an alarm based on said one or more properties.

14. The method as recited in claim 1 further comprising the step of transmitting one or more data elements related to said one or more properties to a local data storage medium.

15. The method as recited in claim 1 further comprising the step of transmitting one or more data elements related to said one or more properties to a remote data storage medium.

16. The method as recited in claim 1 further comprising the step of determining when the supplying of said second fluid has ceased due to depletion of said second fluid.

17. The method as recited in claim 16 further comprising the step of supplying a third fluid substantially similar to said second fluid.

18. The method as recited in claim 1 further comprising the step of cleansing said sensing surface of said fixed optic sensor.

19. The method as recited in claim 1 wherein said fixed optic sensor comprises:
   a light source;
   a sensing surface disposed at an angle to receive at least one light ray emitted from said light source; and
   a photodetector for measuring intensity of a reflected component of said at least one light ray.

20. A system for automatically sensing and controlling beverage quality, comprising:
   a controller means;
   a first valve electrically coupled to said controller means for controlling supply of a first beverage fluid;
   a second valve electrically coupled to said controller means for controlling supply of a second beverage fluid; and
   a fixed optic sensor electrically coupled to said controller means, wherein the fixed optic sensor is operative to sense one or more properties associated with the first and second beverage fluids and cause the controller means to control said first valve and said second valve based on said one or more properties to maintain a precise and predetermined fixed ratio of the beverage fluids as the one or more properties change.

21. The system as recited in claim 20 wherein said fixed optic sensor is a surface plasmon resonance sensor.

22. The system as recited in claim 20 wherein said fixed optic sensor is a refractometer.

23. The system as recited in claim 20 wherein said controller means is a digital signal processing unit.

24. The system as recited in claim 20 wherein said controller means is a microcontroller.

25. The system as recited in claim 20 wherein said first valve is selectively opened and closed according to a prescribed first duty cycle.

26. The system as recited in claim 20 wherein said second valve is selectively opened and closed according to a prescribed second duty cycle.

27. The system as recited in claim 20 wherein the diameter of said first valve is variably increased and decreased.

28. The system as recited in claim 20 wherein said second valve is variably increased and decreased.

29. The system as recited in claim 20 further comprising an alarm device electrically connected to said controller means.

30. The system as recited in claim 20 further comprising a third valve electrically coupled to said controller means for controlling supply of a third fluid.

31. The system as recited in claim 20 further comprising a variable input electrically coupled to said controller means.

32. The system as recited in claim 20 further comprising a local data storage medium electrically coupled to said controller means.

33. The system as recited in claim 20 further comprising a remote data storage medium for receiving one or more data elements transmitted from said controller means unit via a network.

34. The system as recited in claim 20 wherein said fixed optic sensor comprises:
   a light source;
   a sensing surface disposed at an angle to receive at least one light ray emitted from said light source; and
   a photodetector for measuring intensity of a reflected component of said at least one light ray.

35. A system for automatically monitoring and improving beverage quality, comprising:
   a controller means;
   a first valve electrically coupled to said controller means for controlling supply of a first beverage fluid;
   a second valve electrically coupled to said controller means for controlling supply of a second beverage fluid; and
   a fixed optic sensor coupled to said controller means;
   an alarm device electrically connected to said controller means;
   a variable input electrically coupled to said controller means;
   a local data storage medium electrically coupled to said controller means; and
   a remote data storage medium for receiving one or more data elements transmitted from said controller means via a network, wherein the fixed optic sensor is operative to sense one or more properties associated with the first and second beverage fluids and cause the controller means to control said first valve and said second valve based on said one or more properties to maintain a precise and predetermined fixed ratio of the beverage fluids as the one or more properties change.

* * * * *